United States Patent
Schudok et al.

(10) Patent No.: US 7,399,770 B2
(45) Date of Patent: Jul. 15, 2008

(54) THIENO-IMINO ACID DERIVATIVES FOR USE AS MATRIX METALLOPROTEINASE INHIBITORS

(75) Inventors: Manfred Schudok, Eppstein/Ts (DE);
Hans Matter, Langenselbold (DE);
Armin Hofmeister, Oppenheim (DE);
Maxime Lampilas, Saint Cloud (FR)

(73) Assignee: SANOFI-AVENTIS Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/461,189

(22) Filed: Jul. 31, 2006

(65) Prior Publication Data

US 2007/0093482 A1    Apr. 26, 2007

Related U.S. Application Data

(63) Continuation of application No. PCT/EP2005/000417, filed on Jan. 18, 2005.

(30) Foreign Application Priority Data

Jan. 31, 2004   (DE)   ........................ 10 2004 004 974

(51) Int. Cl.
*A61K 31/4365* (2006.01)
*C07D 409/02* (2006.01)
*C07D 495/06* (2006.01)

(52) U.S. Cl. ...................................... 514/301; 546/114
(58) Field of Classification Search ................. 514/301; 546/114

See application file for complete search history.

(56) References Cited

U.S. PATENT DOCUMENTS

| | | | |
|---|---|---|---|
| 5,294,621 A | 3/1994 | Russell | |
| 5,861,510 A | 1/1999 | Piscopio et al. | |
| 6,015,912 A | 1/2000 | Wang et al. | |
| 6,207,672 B1 | 3/2001 | Thorwart | |
| 6,573,277 B2 | 6/2003 | Thorwart | |
| 6,815,440 B2 | 11/2004 | Thorwart | |
| 2003/0130257 A1 | 7/2003 | Sheppeck et al. | |
| 2005/0245505 A1 | 11/2005 | Aszodi | |

FOREIGN PATENT DOCUMENTS

| | | |
|---|---|---|
| EP | 0606046 | 10/1997 |
| WO | WO 94/28889 | 12/1994 |
| WO | WO 96/27583 | 9/1996 |
| WO | WO 03/089416 | 10/2003 |

OTHER PUBLICATIONS

ISR of PCT/EP05/000417.*
Borowski, et al., Ractivity of the Bis(dihydrogen) Complex [RuH2(n2-H2)2(Pcy3)2] toward S-Heteroaromtic Compounds. Catalytic Hydrogenation of Thiophene, Organometallics 2003, 22, 4803-4809.

Busolo, M., et al., The Biphasic Regioselective Hydrogenation of Benzo [b] Thiophene and Quinoline Catalyzed by Ru(II) Species, Derving From The Water Soluble Phosphine TPPTS (Tris-Meta-Sulfonato-Phenylphosphine and Stabilized By Nitrogen Donor Ligands, Journal of Molecular Catalysis A: Chemical 189 (2002) 211-217.
Creemers, E. et al., Matrix Metalloproteinase Inhibition After Myocardial Infarction, Circulation Research 89 (2001), 201-210.
Li Y, et al., Matrix Metalloproteinases in the Progression of Heart Failure Potential Therapeutic Implications, Drugs (2001) 61 (9) 1239-1252.

(Continued)

*Primary Examiner*—Taofiq A Solola
(74) *Attorney, Agent, or Firm*—Ronald G. Ort

(57) ABSTRACT

The invention is directed to a compound of the formula I

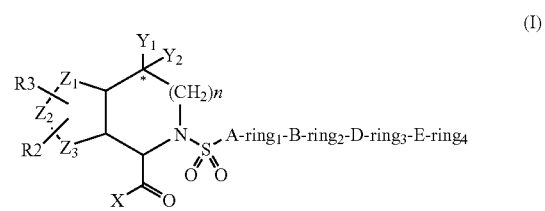

wherein the variables are as defined herein, or
a stereoisomeric form thereof, mixture of stereoisomeric forms, in any ratio, or a salt thereof.

Another aspect of the present invention is directed to a pharmaceutical composition comprising, a pharmaceutically effective amount of one or more compounds of formula I according to claim 1 in admixture with a pharmaceutically acceptable carrier.

The invention is also directed to a method for effecting the prophylaxis and therapy of degenerative joint diseases such as osteoarthroses, spondyloses, cartilage loss following joint trauma or a relatively long period of joint immobilization following meniscus or patella injuries or ligament ruptures, diseases of the connective tissue such as collagenoses, periodontal diseases, wound healing disturbances and chronic diseases of the locomotory apparatus such as inflammatory, immunological or metabolism-associated acute and chronic arthritides, arthropathies, myalgias and disturbances of bone metabolism, for the treatment of ulceration, atheroscleroses and stenoses, and for the treatment of inflammations, cancer diseases, tumor metastasis formation, cachexia, anorexia, cardiac insufficiency and septic shock or for the prophylaxis of myocardial and cerebral infarctions, in a patient in need thereof, comprising administering to the patient a pharmaceutically effective amount of the compound of formula I according to claim 1, or a pharmaceutically acceptable salt, solvate or prodrug thereof.

Furthermore the invention is directed to a method for preparing a compound of formula I.

5 Claims, No Drawings

OTHER PUBLICATIONS

Massova, I., et al., Matrix Metalloproteinases: Structures, Evolution, an Diversification, The FASEB Journal (1998) 12, 1075-1095.

Michaelides, et al., Recent Advances in Matrix Metalloproteinase Inhibitors Research, Current Phamaceutical Design 5 (1999), 787-819.

Skiles, J., et al., The Design, Structure, and Therapeutic Application of Matrix Metalloproteinase, Current Medicinal Chemistry 2001, 8, 425-474.

Sarah J. George, Therapeutic Potential of Matrix Metalloproteinase Inhibitors in Atherosclerosis, Expert Opinion on Investigational Drugs (2000), 9 (5), 993-1007.

T.H. Greene, et al., Protection For the Amino Group, Protective Groups in Organic Synthesis—Carbamates; Wiley-Interscience; 1999; pp. 502-537.

T.H. Greene, et al., Protection for the Carboxyl Group, Protective Groups in Organic Synthesis, Wiley-Interscience; 1999; pp. 369-407.

Yip, et al., Matrix Metalloproteinase Inhibitors: Applications In Oncology, Investigational New Drugs 17 (1999), 387-399.

* cited by examiner

THIENO-IMINO ACID DERIVATIVES FOR USE AS MATRIX METALLOPROTEINASE INHIBITORS

FIELD OF THE INVENTION

The invention relates to novel derivatives of thienyl-containing bicyclic and tricyclic imino acids, to process for preparing them and to their use as pharmaceuticals.

BACKGROUND OF THE INVENTION

In diseases such as osteoarthritis and rheumatism, a destruction of the joint takes place, with this being due, in particular, to the proteolytic breakdown of collagen by collagenases. Collagenases belong to the metalloproteinase (MP) or matrix metalloproteinase (MMP) superfamily. The MMP's form a group of Zn-dependent enzymes which are involved in the biological breakdown of the extracellular matrix (D. Yip et al. in Investigational New Drugs 17 (1999), 387-399 and Michaelides et al. in Current Pharmaceutical Design 5 (1999) 787-819). These MMPs are able, in particular, to break down fibrillar and nonfibrillar collagen and also proteoglycans, both of which are important constituents of the matrix. MMPs are involved in processes of wound healing, of tumor invasion and metastasis migration as well as an angiogenesis, multiple sclerosis and heart failure (Michaelides, page 788; see above). In particular, they play an important role in the breakdown of the joint matrix in arthrosis and arthritis, whether this be osteoarthrosis, osteoarthritis and rheumatoid arthritis.

Furthermore, the activity of the MMPs is essential for many of these processes which play a role in atherosclerotic plaque formation, such as infiltration of inflammatory cells and smooth muscle cell migration, as well as proliferation and angiogenesis (S. J. George, Exp. Opin. Invest. Drugs (2000), 9 (5), 993-1007). In addition, matrix degradation by MMPs can give rise to anything from plaque instabilities to ruptures, with this in turn being able to lead to the clinical symptoms of atherosclerosis, unstable angina pectoris, myocardial infarction or stroke (E. J. M. Creemers et al., Circulation Res. 89, 201-210 (2001)). Seen as a whole, the entire MMP family is able to break down all of the components of the extracellular matrix of the blood vessels; their activities are therefore strictly regulated in normal blood vessels. The increase in MMP activity during plaque formation and plaque instability is brought about by an increase in cytokine-stimulated and growth factor-stimulated gene transcription, an increase in zymogen activation and an imbalance in the MMP/TIMP (tissue inhibitors of metalloproteases) ratio. It therefore appears plausible that MMP inhibition or restoration of the MMP/TIMP balance would be of help in treating atherosclerotic disease. It is also becoming ever clearer that an increase in MMP activity is also at least a contributory cause of other cardiovascular diseases, in addition to atherosclerosis, such as restenosis, dilated cardiomyopathy and the myocardial infarction which has already been mentioned.

In experimental animal models of these diseases, it has been shown that marked improvements, for example with regard to the formation of atherosclerotic lesions, neointima formation, left ventricular remodeling, pumping performance dysfunction or infarction healing, can be achieved by administering synthetic inhibitors. In addition, reduced collagen damage, improved extracellular matrix remodeling and improved structure and function of cardiac muscle and blood vessels have been found when detailed tissue analyses have been carried out in a variety of preclinical studies using MMP inhibitors. Of these processes, the matrix remodeling processes and MMP-regulated fibroses, in particular, are regarded as being important components in the progress of cardiac diseases (infarction) (Drugs 61, 1239-1252 (2001)).

MMPs cleave matrix proteins such as collagen, laminin, proteoglycans, elastic or gelatin and also process (i.e. activate or inactivate), by means of cleaving, a large number of other proteins and enzymes under physiological conditions, which means that they play an important role in the entire organism while being of particular significance in connective tissue and bones.

A large number of different MMP inhibitors have been disclosed (EP 0 606 046; WO 94/28889; WO 96/27583; or Current Medicinal Chemistry 8, 425-74 (2001)).

Following the first clinical studies performed on humans, it has now been found that MMPs give rise to side-effects. The side-effects which are principally mentioned are musculoskeletal pains and arthralgias. The prior art clearly indicates that inhibitors which are more selective are expected to be able to reduce these side-effects (Yip, page 387, see above). Specificity towards MMP-1 is to be particularly emphasized in the connection since these undesirable side-effects evidently occur to a greater degree when MMP-1 is inhibited.

A frequently occurring disadvantage of the known MMP inhibitors is therefore their lack of specificity. Most MMP inhibitors inhibit many MMPs simultaneously because the catalytic domains of the MMPs have similar structures. As a consequence, the inhibitors act in an undesirable manner on the enzymes, including those that have a vital function (Massova I, et al., The FASEB Journal (1998) 12, 1075-1095).

SUMMARY OF THE INVENTION

The invention is directed to a compound of the formula I

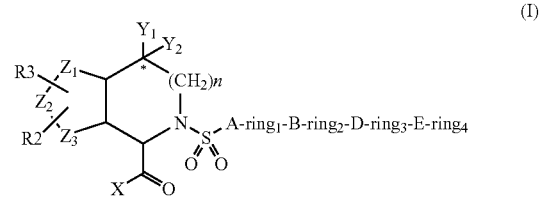

wherein
A is covalent bond or —($C_1$-$C_4$)-alkylene;
B, D and E are independently
  covalent bond,
  —($C_{1-4}$)-alkylene or
  —B1—B2—B3—;
B1 is —($CH_2$)$_v$—;
B3 is —($CH_2$)$_m$—;
B2 is
  —C(=O)—
  —($C_2$-$C_4$)-alkenylene,
  —($C_2$-$C_6$)-alkynylene,
  —S(=O)$_o$—,
  —N(R6)—,
  —N(R6)—C(=Y)—,
  —C(=Y)—N(R6)—,
  —N(R6)—$SO_2$—,
  —$SO_2$—N(R6)—,
  —N(R6)—$SO_2$—N(R6)—,
  —N(R6)—C(=Y)—N(R6)—,
  —O—C(=O)—N(R6)—, —NH—C(=O)—O—,
—O—,
—C(=O)—O—,
—O—C(O)—,
—O—C(O)—O—,
—O—CH$_2$—C(=O)—,
—O—CH$_2$—C(=O)—O—,
—O—CH$_2$—C(=O)—N(R6)—,
—C(=O)—CH$_2$—O—,
—O—C(=O)—CH$_2$—O—,
—N(R6)—C(=O)—CH$_2$—O—,
—O—(CH$_2$)$_s$—O—,
—O—(CH$_2$)$_t$—N(R6)—,
—N(R6)—(CH$_2$)$_u$—O—,
—N(R6)—N(R6)—,
—N=N—,
—N(R6)—CH=N—,
—N=CH—N(R6)—,
—N(R6)—C(R7)=N—, or
—N=C(R7)—N(R6);
v and m are each independently zero, 1 or 2, provided that the sum of v and m is zero, 1 or 2;
R6 is hydrogen atom, methyl or ethyl;
Y is oxygen atom or sulfur atom;
o is zero, 1 or 2;
s is 2 or 3;
t is 2 or 3;
u is 2 or 3;
R7 is —NH—R6;
ring1, ring2 or ring3 are independently
  covalent bond,
  —(C$_6$-C$_{14}$)-aryl optionally substituted independently one, two or three times by G, or
  4- to 15-membered Het ring optionally substituted independently one, two or three times by G;
ring4 is
  —(C$_6$-C$_{14}$)-aryl optionally substituted independently one, two or three times by G,
  4- to 15-membered Het ring optionally substituted independently one, two or three times by G, or
  radical selected from

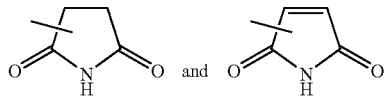

wherein the radical is optionally substituted by one time by G;
G is
  hydrogen atom,
  halogen,
  =O,
  —(C$_1$-C$_6$)-alkyl optionally substituted independently one, two or three times by halogen, —(C$_3$-C$_6$)-cycloalkyl, —(C$_2$-C$_6$)-alkynyl, —(C$_6$-C$_{14}$)-aryl or Het ring,
  —(C$_6$-C$_{14}$)-aryl,
  Het ring,
  —C(=O)—O—R10,
  —C(=S)—O—R10,
  —C(=O)—NH—R11,
  —C(=S)—NH—R11,
  —O—R12,
  —C(=O)—R10,
  —S(=O)$_p$—R12,
  —NO$_2$,
  —CN,
  —N(R15)—R12, or
  —SO$_2$—N(R12)—R16;
R10 is
  —(C$_1$-C$_6$)-alkyl optionally substituted independently one or two times by —(C$_3$-C$_6$)-cycloalkyl, —(C$_2$-C$_6$)-alkynyl, —(C$_6$-C$_{14}$)-aryl or Het ring,
  —(C$_6$-C$_{14}$)-aryl or
  Het ring;
R11 is
  —(C$_1$-C$_6$)-alkyl optionally substituted independently one or two times by —(C$_3$-C$_6$)-cycloalkyl, —(C$_2$-C$_6$-)-alkynyl, —(C$_6$-C$_{14}$)-aryl or Het ring, or
  —(C$_6$-C$_{14}$)-aryl or
  Het ring;
R12 is
  hydrogen atom,
  —(C$_1$-C$_6$)-alkyl optionally substituted independently one, two or three times by halogen, —(C$_3$-C$_6$)-cycloalkyl, —(C$_2$-C$_6$)-alkynyl, —(C$_6$-C$_{14}$)-aryl or Het ring,
  —(C$_6$-C$_{14}$)-aryl,
  Het ring,
  —C(=O)—O—R13,
  —C(=S)—O—R13,
  —C(=O)—NH—R14, or
  —C(=S)—NH—R14;
R13 is
  —(C$_1$-C$_6$)-alkyl optionally substituted independently one or two times by —(C$_3$-C$_6$)-cycloalkyl, —(C$_2$-C$_6$)-alkynyl, —(C$_6$-C$_{14}$)-aryl, or Het ring, or
  —(C$_6$-C$_{14}$)-aryl or
  Het ring;
R14 is
  —(C$_1$-C$_6$)-alkyl optionally substituted independently one or two times by —(C$_3$-C$_6$)-cycloalkyl, —(C$_2$-C$_6$)-alkynyl, —(C$_6$-C$_{14}$)-aryl or Het ring,
  —(C$_6$-C$_{14}$)-aryl or
  Het ring;
p is zero, 1 or 2;
R15 is
  hydrogen atom,
  —(C$_1$-C$_6$)-alkyl, or
  —SO$_2$—(C$_1$-C$_6$)-alkyl wherein the alkyl is optionally substituted by one or two times by —(C$_3$-C$_6$)-cycloalkyl, —(C$_2$-C$_6$)-alkynyl, —(C$_6$-C$_{14}$)-aryl or Het ring;
R16 is
  hydrogen atom,
  —(C$_1$-C$_6$)-alkyl optionally substituted independently one or two times by —(C$_3$-C$_6$)-cycloalkyl, —(C$_2$-C$_6$)-alkynyl, —(C$_6$-C$_{14}$)-aryl or Het ring,
  —C(=O)—O—R8,
  —O—R8, or
  —(C$_3$-C$_6$)-cycloalkyl;
X is —OH or —NH—OH;
n is zero, 1 or 2;

as the constituent structure of the compound is an unsaturated or partially saturated ring containing 5 ring atoms, where one of the ring atoms Z1, Z2 or Z3 is a sulfur atom and the other two ring atoms are carbon atoms that are substituted independently of each other by R2 or R3;

R2 and R3 are independently,
hydrogen atom,
—($C_1$-$C_6$)-alkyl optionally substituted independently one or two times by —($C_3$-$C_6$)-cycloalkyl, —($C_2$-$C_6$)-alkynyl, —($C_6$-$C_{14}$)-aryl or Het ring,
—C(=O)—O—R8,
—O—R8,
—($C_3$-$C_6$)-cycloalkyl,
-halogen,
—$NO_2$, or —CN, or R2 and R3 form, together with the carbon atoms through which they are bonded, a
—($C_6$-$C_{14}$)-aryl ring optionally substituted independently one or two times by G,
—($C_5$-$C_7$)-cycloalkyl ring, or
5-, 6- or 7-membered Het ring optionally substituted one time by G;

R8 is
hydrogen atom,
—($C_1$-$C_6$)-alkyl optionally substituted independently one or two times by —($C_3$-$C_6$)-cycloalkyl, —($C_2$-$C_6$)-alkynyl, —($C_6$-$C_{14}$)-aryl, or Het ring, or one, two, three, four or five times by fluorine,
—($C_6$-$C_{14}$)-aryl or
Het ring;

Y1 and Y2 are each independently,
hydrogen atom,
halogen,
—CN,
—($C_1$-$C_6$)-alkyl optionally substituted independently one, two or three times by halogen, —($C_3$-$C_6$)-cycloalkyl, —($C_2$-$C_6$)-alkynyl, —($C_6$-$C_{14}$)-aryl or Het ring,
—($C_6$-$C_{14}$)-aryl,
Het ring,
—C(=O)—O—R10,
—C(=S)—O—R10,
—C(=O)—NH—R11,
—C(=S)—NH—R11,
—O—R12,
—O—C(=O)—R10,
—C(=O)—R10,
—S(=O)$_w$—R12,
—N(R15)—R12, or
—$SO_2$—N(R12)—R16, or Y1 and Y2 together form
=O,
=S,
=N—R17, or
=N—O—R17, or Y1 and Y2 form, together with the carbon atom through which they are bonded, a
—($C_3$-$C_7$)-cycloalkyl optionally substituted independently one or two times by —($C_1$-$C_6$)-alkyl, —($C_2$-$C_6$)- alkynyl, —($C_3$-$C_6$)-cycloalkyl, —($C_6$-$C_{14}$)-aryl, or halogen,
or
constituent structure of the formula

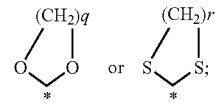

q and r are 2, 3 or 4;
—($CH_2$)$_q$— or —($CH_2$)$_r$— radical optionally substituted independently one or two times by
—($C_1$-$C_6$)-alkyl, —($C_2$-$C_6$)-alkynyl, —($C_3$-$C_6$)-cycloalkyl, —($C_6$-$C_{14}$)-aryl, or halogen;
w is zero, 1 or 2; and
R17 is
hydrogen atom,
—($C_1$-$C_6$)-alkyl optionally substituted independently one or two times by —($C_3$-$C_6$)-cycloalkyl, —($C_2$-$C_6$)-alkynyl, —($C_6$-$C_{14}$)-aryl or Het ring,
—($C_6$-$C_{14}$)-aryl, or
Het ring, or
a stereoisomeric form thereof, mixture of stereoisomeric forms, in any ratio, or a salt thereof.

Another aspect of the present invention is directed to a pharmaceutical composition comprising, a pharmaceutically effective amount of one or more compounds of formula I according to claim 1 in admixture with a pharmaceutically acceptable carrier.

The invention is also directed to a method for effecting the prophylaxis and therapy of degenerative joint diseases such as osteoarthroses, spondyloses, cartilage loss following joint trauma or a relatively long period of joint immobilization following meniscus or patella injuries or ligament ruptures, diseases of the connective tissue such as collagenoses, periodontal diseases, wound healing disturbances and chronic diseases of the locomotory apparatus such as inflammatory, immunological or metabolism-associated acute and chronic arthritides, arthropathies, myalgias and disturbances of bone metabolism, for the treatment of ulceration, atheroscleroses and stenoses, and for the treatment of inflammations, cancer diseases, tumor metastasis formation, cachexia, anorexia, cardiac insufficiency and septic shock or for the prophylaxis of myocardial and cerebral infarctions, in a patient in need thereof, comprising administering to the patient a pharmaceutically effective amount of the compound of formula I, or a pharmaceutically acceptable salt, solvate or prodrug thereof.

Furthermore the invention is directed to a method for preparing a compound of formula I.

DETAILED DESCRIPTION OF THE INVENTION

Definition of the Terms

As used above, and throughout the description of the invention, the following terms, unless otherwise indicated, shall be understood to have the following means:

"Patient" includes human and other mammals.

"Pharmaceutically acceptable salts" refers to the non-toxic, inorganic and organic acid addition salts, and base addition salts, of compounds of the present invention. These salts can be prepared in situ during the final isolation and purification of the compounds.

"Pharmaceutically effective amount" means an amount of compound, or compounds, according to the present invention effective that produces the desired therapeutic effect described herein, such as allergy relieving, or inflammatory relieving effect.

The term "$(C_1-C_6)$-alkyl" is understood as meaning hydrocarbon radicals whose carbon chain is straight-chain or branched and contains from 1 to 6 carbon atoms, for example methyl, ethyl, propyl, isopropyl, butyl, isobutyl, tert-butyl, pentyl, isopentyl, neopentyl, hexyl, 2,3-dimethylbutane or neohexyl.

The term "—$(C_1-C_4)$-alkylene" is understood as meaning hydrocarbon radicals whose carbon chain is straight-chain or branched and contains from 1 to 4 carbon atoms, for example methylene, ethylene, propylene, isopropylene, isobutylene, butylene or tert-butylene. The term "—$(CH_2)_n$—, wherein n is zero, 1 or 2" is understood as meaning a covalent bond when n is zero, the radical methylene when n is 1 and the radical ethylene when n is 2.

The term "—$(C_2-C_4)$-alkenylene" is understood as meaning hydrocarbon radicals whose carbon chain is straight-chain or branched and contains from 2 to 4 carbon atoms and which possess, depending on the chain length, 1 or 2 double bonds, for example ethenylene, propenylene, isopropenylene, isobutenylene or butenylene; provided the possibility exists in principle, the substituents at the double bond can be arrange din an E- or Z-configuration.

The term "—$(C_2-C_6)$-alkynylene" is understood as meaning hydrocarbon radicals whose carbon chain is straight-chain or branched and contains from 2 to 6 carbon atoms and which possess, depending on the chain length, 1 or 2 triple bonds, for example ethynylene, propynylene, isopropynylene, isobutylynylene, butynylene, pentynylene or isomers of pentynylene or hexynylene or isomers of hexynylene.

The term "$(C_3-C_7)$-cycloalkyl" is understood as meaning radicals such as compounds which are derived from 3- to 7-membered monocycles such as cyclopropyl, cyclobutyl, cyclopentyl, cyclohexyl or cycloseptyl.

The term "—$(C_6-C_{14})$-aryl" is understood as meaning aromatic hydrocarbon radicals having from 6 to 14 carbon atoms in the ring. —$(C_6-C_{14})$-Aryl radicals are, for example, phenyl, naphthyl, for example 1-naphthyl and 2-naphthyl, anthryl or fluorenyl. Naphthyl radicals and, in particular, phenyl radicals are preferred aryl radicals.

The term "4- to 15-membered Het ring" or "Het ring" is understood as meaning ring systems which contain from 4 to 15 carbon atoms, which are present in one, two or three ring systems which are linked to each other, and which contain one, two, three or four identical or different heteroatoms selected from oxygen, nitrogen and sulfur. Examples of these Het ring systems are the radicals acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl.

Preferred Het rings are the radicals benzofuranyl, benzimidazolyl, benzoxazolyl, benzothiazolyl, benzothiophenyl, 1,3-benzodioxolyl, quinazolinyl, quinolinyl, quinoxalinyl, chromanyl, cinnolinyl, furanyl; such as 2-furanyl and 3-furanyl; imidazolyl, indolyl, indazolyl, isoquinolinyl, isochromanyl, isoindolyl, isothiazolyl, isoxazolyl, oxazolyl, phthalazinyl, pteridinyl, pyrazinyl, pyrazolyl, pyridazinyl, pyridoimidazolyl, pyridopyridinyl, pyridopyrimidinyl, pyridyl; such as 2-pyridyl, 3-pyridyl or 4-pyridyl; pyrimidinyl, pyrrolyl; such as 2-pyrrolyl and 3-pyrrolyl; purinyl, thiazolyl, tetrazolyl or thienyl; such as 2-thienyl and 3-thienyl.

The term "halogen" is understood as meaning fluorine, chlorine, bromine or iodine.

EMBODIMENTS

An embodiment of the invention furthermore is directed to the compound of the formula I wherein ring1, ring2 or ring3 are independently
covalent bond,
phenyl, naphthyl, 1-napthyl, 2-naphthyl, anthryl or fluorenyl, which is optionally substituted independently one, two or three times by G, or
4- to 15-membered Het ring selected from acridinyl, azepinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl, which is optionally substituted independently one, two or three times by G;

ring4 is
—($C_6$-$C_{14}$)-aryl selected from phenyl, naphthyl, 1-naphthyl, 2-naphthyl, anthryl and fluorenyl, which is optionally substituted independently one, two or three times by G, 4- to 15-membered Het ring selected from acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl, which is optionally substituted independently one, two or three times by G, or radical selected from

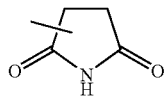 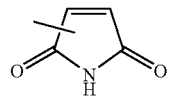

wherein the radical is optionally substituted one time by G;

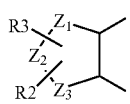

as a constituent structure of the compound is selected from

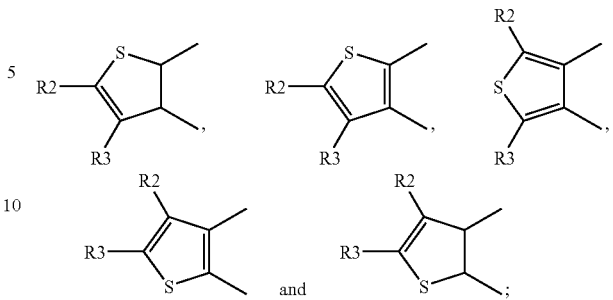

R2 and R3 are independently
hydrogen atom,
—($C_1$-$C_6$)-alkyl optionally substituted independently one or two times by —($C_3$-$C_6$)-cycloalkyl, —($C_2$-$C_6$)-alkynyl, —($C_6$-$C_{14}$)-aryl or Het ring,
C(=O)—O—R8,
—O—R8,
—($C_3$-$C_6$)-cycloalkyl,
-halogen,
—$NO_2$, or
—CN, or R2 and R3 form, together with the carbon atoms through which they are bonded, a
—($C_6$-$C_{14}$)-aryl ring selected from phenyl, naphthyl, 1-naphthyl, 2-naphthyl, anthryl and fluorenyl, which is optionally substituted independently one or two times by G, or
—($C_5$-$C_7$)-cycloalkyl ring, or
5-membered Het ring from selected thiophene, furan, thiazole or oxazole, which is optionally substituted one time by G, or a stereoisomeric form thereof, mixture of stereoisomeric forms, in any ratio, or a salt thereof.

Another embodiment according to the invention is directed to the compound of the formula I wherein B, D and E are independently
covalent bond,
—($C_1$-$C_2$)-alkylene or
—B1—B2—B3—;

B2 is
ethenylene,
ethynylene,
—C(=O)—
—N(R6)—C(=O)—,
—C(=O)—N(R6)—,
—O— or
—S—;

ring1, ring2 or ring3 are independently,
covalent bond,
phenyl or naphthyl, which is optionally substituted independently one or two times by G, or
Het ring selected from dihydrofuranyl, furanyl, pyridyl, pyrimidinyl, pyrrolyl, thiadiazolyl, thiazolyl and thiophenyl, which is optionally substituted independently one or two times by G;

ring4 is
phenyl or naphthyl, which is optionally substituted independently one or two times by G,
Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, or
radical

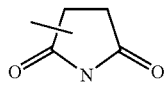

which is optionally substituted once by G:
G is
  hydrogen atom,
  Br, Cl, or F,
  —($C_1$-$C_4$)-alkyl optionally is substituted independently one or two times by F, phenyl, cyclopropyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
  phenyl,
  Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
  —C(=O)—O—R10,
  —C(=O)—NH—R11,
  —O—R12
  —C(=O)—R10,
  —S(=O)$_p$—R12,
  —NO$_2$,
  —CN or
  —N(R15)—R12;
R10 is
  —($C_1$-$C_6$)-alkyl optionally substituted independently one or two times by cyclopropyl, phenyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
  phenyl, or
  Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;
R11 is
  —($C_1$-$C_6$)-alkyl optionally substituted independently one or two times by cyclopropyl, phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
  phenyl, or
  Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;
R12 is
  hydrogen atom,
  —($C_1$-$C_6$)-alkyl optionally substituted independently one, two or three times by halogen, cyclopropyl, phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
  phenyl,
  Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
  —C(=O)—O—R13,
  —C(=S)—O—R13, or
  —C(=O)—NH—R14;
R13 is
  —($C_1$-$C_6$)-alkyl optionally substituted independently one or two times by cyclopropyl, phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, or
  phenyl, or
  Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;
R14 is
  —($C_1$-$C_6$)-alkyl optionally substituted independently one or two times by phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, or
  phenyl, or
  Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;
p is 1 or 2;
R15 is
  hydrogen atom or
  —($C_1$-$C_6$)-alkyl;
n is 1;

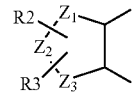

as the constituent structure of the compound is selected from

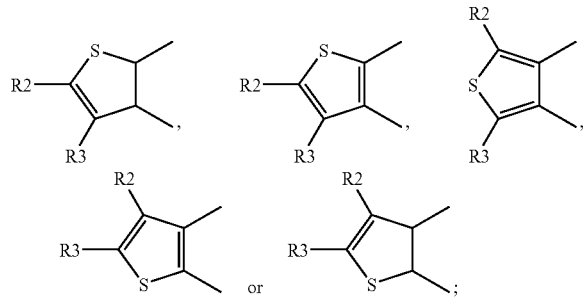

R2 and R3 are hydrogen atom, or

R2 and R3 form, together with the carbon atoms through which they are bonded, a phenyl ring optionally substituted independently one or two times by G;

Y1 and Y2 are identical or different and are, independently of each other, hydrogen atom,

—O—R12,

—(—C(=O)—R10, or

—N(R15)—R12, or

Y1 and Y2 together form

=O,

=N—R17, or

=N—O—R17, or

Y1 and Y2 form, together with the carbon atom through which they are bonded, a constituent structure of the formula

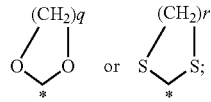

R17 is hydrogen atom,

—(C$_1$-C$_6$)-alkyl optionally substituted independently one or two times by —(C$_3$-C$_6$)-cycloalkyl, —(C$_2$-C$_6$)-alkynyl, phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, phenyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G; and q and r are 2 or 3, or a stereoisomeric form thereof mixture of stereoisomeric forms, in any ratio, or a salt thereof.

Another embodiment of the invention is directed to the compound of the formula I wherein A is a covalent bond or —CH$_2$—CH$_2$—, B, D and E are independently covalent bond, —(C$_1$-C$_2$)-alkylene or

—B1—B2—B3—;

B2 is

—C(=O)— ethynylene,

—S—,

—N(R6)—C(=O)—,

—C(=O)—N(R6)—, or

—O—;

R6 is hydrogen atom ring1, ring2 or ring3 are independently, covalent bond, phenyl which is optionally substituted independently one or two times by G, or Het ring is selected from furanyl, pyridyl, pyrimidinyl and thiophenyl, which is optionally substituted independently one or two times by G, ring4 is phenyl and is optionally substituted independently one or two times by G, Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, or radical

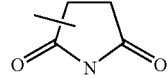

wherein the radical is optionally substituted independently one time by G;

G is hydrogen atom,

Br, Cl or F,

—(C$_1$-C$_4$)-alkyl optionally substituted independently one, two or three times by Br, Cl, F, —C$_3$— cycloalkyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl, Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,

—C(=O)—O—R10,

—C(=O)—NH—R11,

—O—R12,

—C(O)—R10,

—S(O)$_p$—R12,

—NO$_2$,

—CN or

—N(R15)—R12;

R10 is

—(C$_1$-C$_6$)-alkyl optionally substituted independently one or two times by cyclopropyl, phenyl or Het ring selected from benzofuranyl, dibenzofuranyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl, or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G;

R11 is

—($C_1$-$C_6$)-alkyl optionally substituted independently one or two times by cyclopropyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl, or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G;

R12 is hydrogen atom,

—($C_1$-$C_6$)-alkyl optionally substituted independently one, two or three times by halogen, cyclopropyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl, Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,

—C(=O)—O—R13

—C(=S)—O—R13, or

—C(=O)—NH—R14;

R13 is

—($C_1$-$C_6$)-alkyl optionally substituted one or two times by cyclopropyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, R14 is —($C_1$-$C_6$)-alkyl optionally substituted independently one or two times by phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G;

p is zero, 1 or 2;

R15 is hydrogen atom or

—($C_1$-$C_6$)-alkyl;

X is —NH—OH;

n is 1;

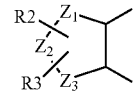

as constituent structure of the compound is selected from

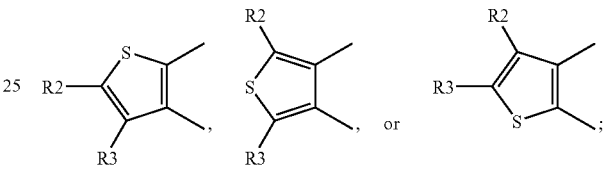

R2 and R3 are hydrogen atom, or

R2 and R3 form, together with the carbon atoms through which they are bonded, a phenyl ring optionally substituted independently one or two times by G, Y1 and Y2 are each independently hydrogen atom,

—O—R12,

—O—C(O)—R10, or

—N(R15)—R12, or

Y1 Y2 form together =O, or

Y1 and Y2 form, together with the carbon atom through which they are bonded, a constituent structure of the formula

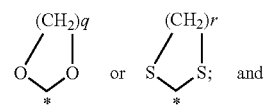

q and r are 2 or 3, or a stereoisomeric form thereof, mixture of stereoisomeric forms, in any ratio, or a salt thereof.

Another embodiment of the invention is directed to the compound

N-(hydroxy)-2-(4'-chlorobiphenyl-4-sulfonyl)-4-hydroxy-1,2,3,4-tetrahydrobenzo[4,5]thieno[3,2-c]pyridine-1-carboxamide, or salt thereof.

Acidic or basic products of the compound of the formula I can be present in the form of their salts or in free form. Preference is given to pharmaceutically acceptable salts, for example alkali metal salts or alkaline earth metal salts or hydrochlorides, hydrobromides, sulfates, hemisulfates, all possible phosphates as well as salts of the amino acids, of natural bases or of carboxylic acids. The preparation, in accordance with process step d), of pharmaceutically acceptable salts from compounds of the formula I, including their stereoisomeric forms, which are capable of salt formation is effected in a manner which is known per se. The compounds of the formula I form stable alkali metal salts, alkaline earth metal salts or ammonium salts, which are substituted where appropriate, with basic reagents such as hydroxides, carbonates, hydrogencarbonates or alkoxides as well as ammonia or organic bases, for example trimethylamine, triethylamine, ethanolamine, diethanolamine, triethanolamine or trometamol or else basic amino acids, for example lysine, ornithine or arginine. If the compounds of formula I possess basic groups, stable acid addition salts can also be prepared using strong acids. Both inorganic and organic acids, such as hydrochloric acid, hydrobromic acid, sulfuric acid, hemisulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, 2-hydroxyethanesulfonic acid, acetic acid, oxalic acid, tartaric acid, succinic acid, glycerophosphoric acid, lactic acid, malic acid, adipic acid, citric acid, fumaric acid, maleic acid, gluconic acid, glucuronic acid, palmitic acid or trifluoroacetic acid are suitable for this purpose.

The invention furthermore relates to a process for preparing the compound of the formula I and/or a stereoisomeric form of the compound of the formula I and/or a pharmaceutically acceptable salt of the compound of the formula I, which comprises a) reacting a compound of the generic formula IV,

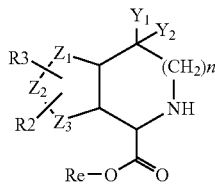

(VII)

wherein Re is a hydrogen atom or an ester protecting group and n, $Y_1$, $Y_2$, $Z_1$, $Z_2$, $Z_3$, $R^2$ and $R^3$ are defined as for the compound of formula I, with a compound of the formula V,

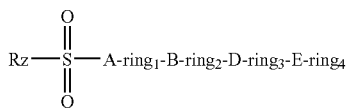

(V)

wherein A, B, D, E and ring1 ring2, ring3, ring4 are defined as in the compound of formula I and wherein Rz is chlorine atom, imidazolyl or OH, in the presence of a base or after silylating with a suitable silylating agent or using a suitable dehydrating agent in the case where Rz=OH, to give a compound of the formula VI,

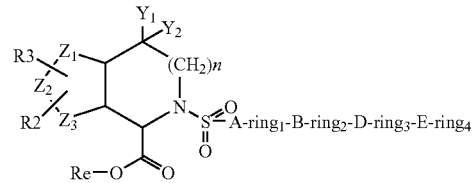

(VI)

wherein A, B, D, E, Re and ring1, ring2, ring3 and ring4 are defined as above, and b) in the case where Re=ester, reacting a compound of the formula VI prepared in accordance with a) with an alkali metal hydroxide such as NaOH or LiOH, and then treating it with acid, to give the carboxylic acid of the formula I according to the invention wherein X=OH (corresponds to VII), with, where appropriate, modifications also having been made previously in one of the side chains of the rings ring1-ring4; or said ester being converted into the free carboxylic acid VII

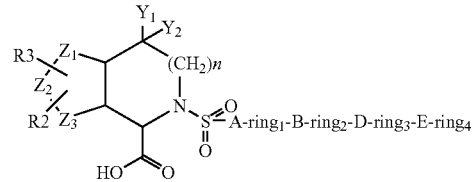

(VII)

by being treated with a mineral acid such as hydrochloric acid and this free carboxylic acid VII then being converted into the hydroxamic acid according to the invention, wherein X=NH—OH, of the formula I, c) a compound of the formula I prepared in accordance with a), or a suitable precursor of the formula I, which appears in enantiomeric forms due to its chemical structure being separated into the pure enantiomers by means of forming salts with enantiomerically pure acids or bases, chromatography or chiral stationary phases or derivatization using chiral enantiomerically pure compounds such as amino acids, separation of the resulting diastereomers and elimination of the chiral auxiliary groups, or d) the compound of the formula I prepared in accordance with method b) or c) being either isolated in free form or, when acidic or basic groups are present, converted into pharmaceutically acceptable salts.

The syntheses of the basic skeletons of the compounds according to the invention are described in the literature. It is possible to modify these basic skeletons extensively and analogous methods are used to prepare the modified basic skeletons.

For example, methyl 4,5,6,7-tetrahydrothieno[3,2-c]pyridine-4-carboxylate is synthesized, as described in EP 0366327, by means of Pictet-Spengler cyclization, by reacting 2-(2-thienyl)ethylamine with methyl glyoxylate. This compound is also prepared in Heterocycles 1981, pp. 35-7.

4,5,6,7-Tetrahydrothieno[2,3-c]pyridine-7-carboxylic acids are described, for example, in EP 230922 and EP 174571 and, in substituted form, in WO 2002100860. In this case, too, it is also possible to use Pictet-Spengler-type cyclizations of 2-(3-thienyl)ethylamines with corresponding glyoxylates, or a combination of the alkylation of suitable precursors and Friedel-Crafts acylation.

If substituent-containing starting compounds such as 4- and/or 5-methylthienylethylamines, are used instead of the unsubstituted thienylethylamines, correspondingly substituted cyclic starting compounds are then obtained. Substituents can also be present on the ethylamine side chain such that the corresponding, substituted tetrahydrothienopyridines are then obtained. It is also possible to use substituted or unsubstituted benzothienylethylamines in cyclization reactions. Preference is given to using the 4-keto precursors as starting compounds for preparing the 4-hydroxy compounds according to the invention that are described in more detail in the example. The keto starting compounds that are protected at the nitrogen and at the carboxylic acid are synthesized in a manner that is analogous, for example, to that described in detail in WO 2002100860.

4,5,6,7-Tetrahydrothieno[3,4-c]pyridines are described, for example, in U.S. Pat. No. 5,294,621. Analogous syntheses using appropriate starting compounds lead to the 4,5,6,7-tetrahydrothieno[3,4-c]pyridine-4-carboxylic acids. In this case, preference is given to starting compounds which are substituted by R2 or R3 at the thiophene, for example thienyl-3-alkylamines, which can be used in said cyclization reaction and lead to the corresponding regiochemistry of the newly formed bicyclic system. 2-Substituted thiophene-3-aldehydes, which are prepared in accordance with known methods and which are further reacted to give the alkylamines, are, for example, used as starting compounds for preparing these thienylalkylamines.

The groups which are used in "Protective Groups in Organic Synthesis", T. H. Greene, P. G. M. Wuts, Wiley-Interscience, 1999, as protecting groups for esters can be employed as the ester protecting group Re. Examples of preferred ester protecting groups are methyl, ethyl, isopropyl, tert-butyl and benzyl.

Under certain conditions, it can be appropriate to use type IV compounds in the N-protected state. For example, it is easier to purify compounds which are protected in this way than it is to purify the free imino acids; the protected compounds may also sometimes be more readily used for preparing the enantiomerically pure or diastereomerically pure compounds. The compounds described in "Protective Groups in Organic Synthesis", T. H. Greene, P. G. M. Wuts, Wiley-Interscience, 1999, can be used as protecting groups for the amino group. Examples of preferred amino or imino protecting groups are Z, Boc, Fmoc, Aloc, acetyl, trifluoroacetyl, benzoyl, benzyl and the like.

The starting compounds and reagents employed can either be prepared in accordance with known methods or obtained commercially.

The reactions take place as described, for example, in WO 97/18194. The reaction in accordance with process step a) takes place in the presence of a base such as KOH, NaOH, LiOH, N-methylmorpholine (NMM), N-ethylmorpholine (NEM), triethylamine (TEA), diisopropylethylamine (DIPEA), pyridine, collidine, imidazole or sodium carbonate, in solvents such as tetrahydrofuran (THF), dimethylformamide (DMF), dimethylacetamide, dioxane, acetonitrile, toluene, chloroform or methylene chloride or else in the presence of water. When the reaction is carried out using silylating agents, N,O-bis(trimethylsilyl)acetamide (BSA) or N,O-bis(trimethylsilyl)trifluoroacetamide (BSTFA) is, for example, used for silylating the imino acid in order to subsequently carry out the sulfonamide formation.

Modifications in the F side chain mean that, for example, a nitro group is hydrogenated using the metal catalyst Pd/C or reacted with $SnCl_2$ or Zn under standard conditions and the resulting amino group can then be subjected to further modification, for example by reaction with carbonyl chlorides, sulfonyl chlorides, chloroformic esters, isocyanates, isothiocyanates or other reactive or activatable reagents in order to arrive at the precursors of the compounds of formula I according to the invention. In this case, it is frequently advantageous for Re in compound VI to be an ester since side reactions can be expected if the carboxylic acid is unprotected.

If it arises as a mixture of diastereomers or enantiomers, or accrues as mixtures thereof in the chosen synthesis, the compound of the formula I is separated, in process step c), into the pure stereoisomers either by means of chromatography on a support material which is chiral, where appropriate, or, if the racemic compound of the formula I is capable of salt formation, by means of the fractional crystallization of the diastereomeric salts which are formed using an optically active base or acid as auxiliary substance. Examples of suitable chiral stationary phases for the thin layer chromatographic or column chromatographic separation of enantiomers are modified silica gel supports (what are termed Pirkle phases) and high molecular weight carbohydrates such as triacetyl cellulose. Gas chromatographic methods on chiral stationary phases can also be used for analytical purposes, following appropriate derivatization known to the skilled person. For the purpose of separating the racemic carboxylic acids into the enantiomers, the diastereomeric salts of differing solubility are formed using an optically active base which can usually be obtained commercially, such as (−)-nicotine, (+)- and (−)-phenylethylamine, quinine bases, L-lysine or L- or D-arginine, the more sparingly soluble component is isolated as a solid, the more readily soluble diastereomer is precipitated from the mother liquor and the pure enantiomers are isolated from the diastereomeric salts which have been obtained in this way. The racemic compounds of the formula I which contain a basic group such as an amino group can be converted into the pure enantiomers in what is in principle the same manner using optically active acids, such as (+)-camphor-10-sulfonic acid, D- and L-tartaric acid, D- and L-lactic acid and (+) and (−)-mandelic acid. It is also possible to convert chiral compounds which contain alcohol or amine functions into the corresponding esters or amides using appropriately activated or, where appropriate, N-protected enantiomerically pure amino acids or, conversely, to convert chiral carboxylic acids into the aides using carboxy-protected enantiomerically pure amino acids or into the corresponding chiral esters using enatiomerically pure hydroxycarboxylic acids such as lactic acid. The chirality of the amino acid residue or alcohol residue which has been introduced in enatiomerically pure form can then be used for separating the isomers by means of separating the diastereomers, which are now present, by means of crystallization or chromatography on suitable stationary phases and, after that, using suitable methods to once again eliminate the chiral molecule which has been entrained.

Furthermore, the possibility arises, in the case of some of the compounds according to the invention, of using diastereomerically pure or enantiomerically pure starting compounds for preparing the skeletal structures. This makes it possible, where appropriate, to also use different or simplified methods for purifying the end products. These starting compounds were prepared previously in enantiomerically pure form or diastereomerically pure form using methods known from the literature. This can mean, in particular, either that enantioselective methods are used in synthesizing the basic skeletons or that an enantiomeric (or diasteromeric) separation is carried out at an early stage in the synthesis rather than waiting until the stage of the end products. These separations can also be simplified by proceeding in two or more steps. For example, it is possible, in the case of a structure of the formula I according to the invention where Y1 and Y2 together=O and n=1, to carry out a racemate resolution using one of said methods and then only to carry out a reduction to the alcohol using the enantiomerically pure keto compounds. It is either possible to use methods which permit diastereoselective reduction or it is now easier to achieve a separation of diastereomers using conventional methods.

Another possibility of synthesizing enantiomerically pure or diastereomerically pure cyclic compounds is that of using acyclic starting compounds which are suitably substituted chirally in order to use the chiral substituents to induce chirality at other chiral centers. For example, chiral glyoxylic esters (such as menthol esters) could be used in Pictet-Spengler cyclizations employing, for example, thienylethylamines.

2-3-Dihydrothiophene derivatives can be prepared from the corresponding thiophenes. A large number of methods are known to the skilled person. More recent methods are described, for example, in Organometallics 22(23), 4803 (2003) or in J. of Molecular Catalysis A: Chemical 182 (2), 211-17 (2002). These methods are used successfully when R2 and R3 together form an aryl system when Z1 or Z2 is sulfur. This makes it possible to achieve a hexahydropyridine system. An exemplary compound is 1,2,3,4,4a,9b-hyexahydrobenzo[4,5]thieno[3,2-c]pyridine-1-carboxylic acid.

The invention also relates to pharmaceutical compositions comprising a pharmaceutically effective amount of at least one compound of the formula I or a pharmaceutically acceptable salt thereof, and/or an optionally stereoisomeric form of the compound of the formula I, together with a pharmaceutically acceptable carrier, additive and/or other active compounds and auxiliary substances.

On account of their pharmacological properties, the compounds according to the invention are suitable for the selective prophylaxis and therapy of all those diseases whose course involves an increase in the activity of the metalloproteinases. These diseases include degenerative joint diseases such as osteoarthroses, spondyloses, cartilage loss following joint trauma or a relatively long period of joint immobilization following meniscus or patella injuries or ligament ruptures. The diseases also include diseases of the connective tissue such as collagenoses, periodontal diseases, wound healing disturbances and chronic diseases of the locomotory apparatus such as inflammatory, immunological or metabolism-associated acute and chronic arthritides, arthropathies, myalgias and disturbances of bone metabolism. The compounds of the formula I are further suitable for treating ulceration, atherosclerosis and stenoses. In addition, the compounds of the formula I are suitable for treating inflammations, cancer diseases, tumor metastasis formation, cachexia, anorexia, cardiac insufficiency and septic shock. The compounds are also suitable for the prophylaxis of myocardial and cerebral infarctions.

The compound according to the invention can be administered by means of oral, inhalative, rectal or transdermal administration or by means of subcutaneous, intraarticular, intraperitoneal or intravenous injection. Oral administration is preferred.

The invention also relates to a process for producing a pharmaceutical which comprises bringing at least one compound of the formula I, together with a pharmaceutically suitable and physiologically tolerated excipient and, where appropriate, other suitable active compounds, additives or auxiliary substances, into a suitable form for administration.

Examples of suitable solid or galenic preparation forms are granules, powders, sugar-coated tablets, tablets, (micro)capsules, suppositories, syrups, juices, suspensions, emulsions, drops or injectable solutions, and also preparations giving a protracted release of active compound, in the production of which use is made of customary adjuvants such as carrier substances, disintegrants, binders, coating agents, swelling agents, glidants, lubricants, flavorings, sweeteners and solubilizers. Frequently employed auxiliary substances which may be mentioned are magnesium carbonate, titanium dioxide, lactose, mannitol and other sugars, talc, milk protein, gelatin, starch, cellulose and its derivatives, animal and vegetable oils such as cod liver oil, sunflower oil, peanut oil or sesame oil, polyethylene glycol and solvents such as sterile water and monohydric or polyhydric alcohols such as glycerol.

The pharmaceutical preparations are preferably produced, and administered, in dosage units with each unit containing, as the active constituent, a defined dose of the compound of the formula I according to the invention. In the case of solid dosage units, such as tablets, capsules, sugar-coated tablets or suppositories, this dose can be up to about 1000 mg, preferably, however, from about 50 to 300 mg, and, in the case of injection solutions in ampoule form, it can be up to about 300 mg, preferably, however, from about 10 to 100 mg.

Depending on the activity of the compound in accordance with formula I, daily doses of from about 2 mg to 1000 mg of active compound, preferably of from about 50 mg to 500 mg, are indicated for treating an adult patient of about 70 kg in weight. However, higher or lower daily doses may also possibly be appropriate. The daily dose can be administered either by means of a once-only administration in the form of a single dosage unit or else of several smaller dosage units or by means of the repeated administration of subdivided doses at defined intervals.

EXAMPLES

End products are as a rule determined by means of mass-spectroscopic methods (FAB MS and ESI MS) and $^1$H NMR (400 MHz, in DMSO-D6); the main peak or the two main peaks is/are given on each occasion. Temperatures are given in degrees Celsius; RT denotes room temperature (from 21° C. to 24° C.). Abbreviations employed are either explained or correspond to the customary conventions.

The invention is explained in more detail below with the aid of examples.

General Protocol 1: Sulfonamide from sulfonyl chloride and carboxylic acid

The carboxylic acid (6.45 mmol) was dissolved in 20 ml of dimethylformamide (DMF) after which 3 equivalents of a 3N solution of NaOH (6.45 ml) were added at 0° C. After 10 min, a solution of the arylsulfonyl chloride (1.1 equivalents, 7.1 mmol) in from 10 to 15 ml of DMF was added slowly dropwise; after room temperature (RT) had been reached, the mixture was stirred further for a maximum of 12 hours (h) at temperatures between 20° C. and 80° C. The precise time depends on when conversion is complete, with this being established by means of mass spectroscopy. After that, the solvent was removed under reduced pressure. Aqueous working-up (extracting by shaking with 1N HCl and a saturated solution of NaCl, drying of the organic phase such as ethyl acetate, methylene chloride or chloroform with magnesium sulfate or sodium sulfate, and after that inspissation) then took place. The crude product was either subjected to further reaction directly or purified by chromatography.

General Protocol 2: Sulfonamide from Sulfonyl Chloride and Carboxylic Acid

The carboxylic acid was dissolved in 0.5-2 molar NaOH, where appropriate in the added presence of 10-50% tetrahydrofuran (THF) or DMF. Acid chloride (1-1.2 equivalents, preferably 1.1) was dissolved in THF (concentration 0.05 to 1 M) and slowly added dropwise. 2 N NaOH was automatically added, at RT, on an autotitrator for the purpose of maintaining a constant pH. Set pH: from 8 to 12, preferably from 9 to 11. After the reaction had come to an end, as recognizable by no further NaOH being consumed, the organic cosolvent was removed on a rotary evaporator; ethyl acetate was added to the aqueous solution or suspension, which was then acidified with 1N HCl. After the organic phase had been separated off and the aqueous phase had been extracted once again with ethyl acetate, the organic phases were combined and dried over sodium sulfate; the solvent was then removed under reduced pressure. The crude product was either subjected to further reaction directly or purified by chromatography.

General Protocol 3: Sulfonamide from Sulfonyl Chloride and Carboxylic Acid.

This protocol is particularly suitable for reacting biphenylethylsulfonyl chloride, or similar sulfonyl chlorides which are more hydrolysis-labile, with iminocarboxylic acids.

8 mmol of the imino acid were dissolved or suspended in 30 ml of acetonitrile. 2.3 g (9 mmol) of BSTFA (bis(trimethylsily)trifluoroacetamide) were added, at RT and under an inert gas ($N_2$), and the mixture was heated under reflux for 2 h. 2.84 g (9 mmol) of 4-chlorobiphenylethanesulfonyl chloride, dissolved in 30 ml of acetonitrile, were added to this solution, which was then heated once again for 3 h under reflux conditions. After the reaction mixture had cooled down, aqueous 1 N HCl was added and the whole was stirred for 1 h; the solvent was removed under reduced pressure on a rotary evaporator after which ethyl acetate or chloroform was added and the organic phase was separated off; this latter was extracted with a saturated solution of NaCl, dried over sodium sulfate and inspissated under reduced pressure. Depending on its purity, the reaction product could either be subjected directly to further reaction or had to be first of all purified by means of silica gel chromatography.

General Protocol 4: Preparing the Hydroxamic Acid from Carboxylic Acid by way of Chloroformate Activation The sulfonated carboxylic acid was dissolved in 10 ml of DMF, after which 1.1 equivalents of ethyl chloroformate, 2.2 equivalents of N-ethylmorpholine and, after a preactivation time of from 30 min to 1 h, 3 equivalents of trimethylsilylhydroxylamine were added at 0° C. After the mixture had been heated at 80° C. for at least 4 h, the solvent was removed under reduced pressure and the crude product was purified using chromatographic methods.

General Protocol 5: Preparing Hydroxamic Acid by by way of the corresponding Carbonyl Chloride The sulfonated carboxylic acid was initially introduced in dry chloroform (ethanol-free) (about 5 ml for 0.5 mmol) after which 3 equivalents of oxalyl chloride were added at RT. The mixture was then warmed at 45° C. for about 30 min. In order to monitor the chloride formation, a small sample was removed from the reaction flask and treated with a little benzylamine in THF. Complete reaction was identified by the quantitative formation of benzylamide, with the carboxylic acid no longer being detectable (monitoring by means of HPLC-MS). It may be necessary to warm for a longer period or to heat under reflux conditions. After that, the solvent was distilled off under reduced pressure and the residue was taken up several times in dry toluene and rotary evaporated once again. The acid chloride was now once again taken up in chloroform (10 ml per 0.5 mmol) and treated, at RT, with 3 equivalents of O-trimethylsilylhydroxylamine. After a reaction period of at least 30 min (reaction monitored by means of HPLC-MS), the reaction mixture was evaporated under reduced pressure and the residue was purified directly by chromatography.

Special Protocols 2-(4'-Chlorobiphenyl-4-sulfonyl)-4-hydroxy-1,2,3, 4-tetrahydrobenzo[4,5]thieno[3,2-c]pyridine-1-carboxylic acid hydroxyamide Step 1: 2-tert-butyl 1-ethyl 4-hydroxy-3,4-dihydro-1H-benzo[4,5]thieno[3,2-]pyridine-1,2-dicarboxylate 2-tert-Butyl 1-ethyl 4-oxo-3,4-dihydro-1H-benzo[4,5]thieno[3,2-c]pyridine-1,2-dicarboxylate (1 g, 2.6 mmol) was dissolved in 30 ml of THF after which sodium borohydride (202 mg, 5.3 mmol) was added at RT. 10 drops of methanol were added and the mixture was stirred at RT for 4 h. 2 ml of 1 M HCl were then added and the mixture was evaporated under reduced pressure in order to remove the THF. After ethyl acetate had been added, the aqueous phase was separated off and the organic phase was washed with a saturated solution of NaCl, dried over sodium sulfate and evaporated under reduced pressure. The resulting residue (0.963 g) was subjected directly to further reaction.

Step 2: 4-Hydroxy-3,4-dihydro-1H-benzo[4,5]thieno [3,2-c]pyridine-1-carboxylic acid The residue (0.96 g, 2.6 mmol) obtained in step 1 was treated with 30 ml of TFA/methylene chloride 1:2 at RT for one hour in order to eliminate the Boc protecting group, after which the solvent was removed under reduced pressure; the residue was then treated directly with sodium hydroxide (0.7 ml, 2 molar) in 3 ml of THF in order to cleave the ester. The mixture was stirred overnight and evaporated after the reaction had been checked by means of HPLC-MS. The resulting residue was subjected to further reaction.

Step 3:2-(4'-Chlorobiphenyl-4-sulfonyl)-4-hydroxy-1,2,3,4-tetrahydrobenzo[4,5]thieno[3,2-c]pyridine-1-carboxylic acid The product of the previous step (342 mg, 1.33 mmol) was taken up in 10 ml of THF and, after 4 ml of sodium hydroxide solution (1 molar) or 4-chlorobiphenyl-4'-sulfonyl chloride (420 mg, 1.46 mmol) had been added, the mixture was stirred overnight. The solvent was then removed under reduced pressure and the residue was taken up in ethyl acetate; this solution was then extracted by shaking with dilute HCL or a saturated solution of NaCl. After drying over sodium sulfate, the solvent was removed under reduced pressure and the resulting product was subjected to further reaction.

Step 4—End product: 2-(4'-Chlorobiphenyl-4-sulfonyl)-4-hydroxy-1,2,3,4-tetrahydrobenzo[4,5]thieno[3,2-c]pyridine-1-carboxylic acid hydroxyamide The carboxylic acid from step 3 (239 mg, 0.49 mmol) was dissolved in 4 ml of THF. After that, ethyl chloroformate (64 mg, 0.59 mmol) and N-ethylmorpholine (79.7 mg, 0.69 mmol) were added at 0° C. and preactivation was carried out at this temperature for one hour. O-Trimethylsilylhydroxylamine (208 mg, 1.98 mmol) was then added and the mixture was stirred overnight at from 0° C. to RT. The solvent was removed under reduced pressure and the residue was taken up in ethyl acetate; this solution was extracted by shaking with dilute HCl, water and sodium carbonate solution. The residue was dissolved, for direct preparative RP-HPLC, in a small quantity of a mixture of acetonitrile, water and 0.01% trifluoroacetic acid. Resulting fractions were pooled, acetonitrile was removed under reduced pressure and the remaining aqueous phase was freeze-dried. Yield: 4.5 mg; unreacted carboxylic acid and other, not specifically characterized, byproducts are obtained in addition. Analytical data are given in Table 1.

0.3 mmol of the substrate/l has been added. The enzyme activity is expressed as increase in extinction/minute.

The inhibitor effect is calculated as percentage inhibition in accordance with the following formula:

% inhibition=100−[(increase in extinction/minute in reaction 2)/(increase in extinction/minute in reaction 1)×100].

The $IC_{50}$, i.e. the inhibitor concentration which is required to inhibit the enzyme activity by 50%, is determined graphically by plotting the percentage inhibitions at different inhibitor concentrations. The buffer solution contains 0.05% Brij (Sigma, Deisenhofen, Germany) and also 0.1 mol of Tris/HCl/l, 0.1 mol of NaCl/l and 0.01 mol of $CaCl_2$/l (pH=7.5).

The enzyme solution contains 2.5 μg of the enzyme domain/ml.

The substrate solution contains 0.3 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$ (Bachem, Heidelberg, Germany)/l.

TABLE 1

| Example | Structure | Molar mass | ES⁻ | $^1$H NMR |
|---------|-----------|------------|-----|-----------|
| 1 | [structure: 2-(4'-Chlorobiphenyl-4-sulfonyl)-4-hydroxy-1,2,3,4-tetrahydrobenzo[4,5]thieno[3,2-c]pyridine-1-carboxylic acid hydroxyamide] | 515.01 | 513.21 | 3.84 (m, 1H); 4.03 (m, 1H); 4.60 (m, 1H); 5.50 (s, 1H); 7.35-8.0 (mm, 12H); 9.2 (s, br, 1H); 11.5 (s, 1H). |

Pharmacological Examples

Determining the enzymatic activity of the catalytic domain of human collagenase-1 (MMP-1). This protein is obtained as an inactive proenzyme from Biocol, Potsdam (catalog No. MMP1).

Activation of the Proenzyme:

2 parts by volume of proenzyme are incubated, at 37° C. for 1 hour, with 1 part by volume of APMA solution. The APMA solution is prepared from a 10 mmol/l solution of p-aminophenylmercuric acetate in 0.1 mmol/l NaOH by diluting with 3 parts by volume of Tris/HCl buffer pH 7.5 (see below). The pH is adjusted to between 7.0 and 7.5 by adding 1 mmol/l HCl. After the enzyme has been activated, it is diluted with the Tris/HCl buffer down to a concentration of 2.5 μg/ml. In order to measure the enzyme activity, 10 μl of enzyme solution are incubated, for 15 minutes, with 10 μl of a 3% (v/v) buffered solution of dimethyl sulfoxide (reaction 1). In order to measure the enzyme inhibitor activity, 10 μl of enzyme solution are incubated with 10 μl of a 3% (v/v) buffered dimethyl sulfoxide solution which contains the enzyme inhibitor (reaction 2).

Both in the case of reaction 1 and in the case of reaction 2, the enzyme reaction is monitored by fluorescence spectroscopy (328 nm (extinction)/393 nm (emission)) after 10 μl of a 3% (v/v) aqueous solution of dimethyl sulfoxide which contains Preparation, and determination of the enzymatic activity, of the catalytic domains of human stromelysin (MMP-3) and neutrophil collagenase (MMP-8).

The two enzymes, i.e. stromelysin (MMP-3) and neutrophil collagenase (MMP-8), were prepared in accordance with Ye et al. (Biochemistry; 31 (1992) pages 11231-11235). In order to measure the enzyme activity, or the enzyme inhibitor effect, 10 μl of enzyme solution were incubated, for 15 minutes, with 10 μl of a 3% (v/v) buffered solution of dimethyl sulfoxide which contained the enzyme inhibitor, where appropriate. After 10 μl of a 3% (v/v) aqueous solution of dimethyl sulfoxide containing 1 mmol of the substrate/l had been added, the enzyme reaction was monitored by fluorescence spectroscopy (328 nm (ex)/393 nm (em)).

The enzyme activity is expressed as increase in extinction/minute. The $IC_{50}$ values listed in table 2 were determined as being those inhibitor concentrations which in each case led to a 50% inhibition of the enzyme.

The buffer solution contained 0.05% Brij (Sigma, Deisenhofen, Germany) and also 0.1 mol of Tris/HCl/l, 0.1 mol of NaCl/l, 0.01 mol of $CaCl_2$/l and 0.1 mol of piperazine-N,N'-bis[2-ethanesulfonic acid]/l (pH=7.5).

The MMP-3 enzyme solution contained 2.3 μg/ml, while the MMP-8 enzyme solution contained 0.6 μg/ml, of one of the enzyme domains prepared in accordance with Ye et al. The substrate solution contained 1 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH$_2$ (Bachem, Heidelberg, Germany)/l.

Determining the enzymatic activity of the catalytic domain of human collagenase-3 (MMP-13). This protein was obtained as inactive proenzyme from INVITEK, Berlin (catalog No. 30 100 803).

Activation of the Proenzyme:

2 parts by volume of proenzyme were incubated, at 37° C. for 1.5 hours, with 1 part by volume of APMA solution. The APMA solution was prepared from a 10 mmol/l solution of p-aminophenylmercuric acetate in 0.1 mmol/l NaOH by diluting with 3 parts by volume of Tris/HCl buffer pH 7.5 (see below). The pH was adjusted to between 7.0 and 7.5 by adding 1 mmol/l HCl. After the enzyme had been activated, it was diluted with the Tris/HCl buffer down to a concentration of 1.67 µg/ml.

In order to measure the enzyme activity, 10 µl of enzyme solution were incubated, for 15 minutes, with 10 µl of a 3% (v/v) buffered solution of dimethyl sulfoxide (reaction 1). In order to measure the enzyme inhibitor activity, 10 µl of enzyme solution were incubated with 10 µl of a 3% (v/v) buffered solution of dimethyl sulfoxide which contained the enzyme inhibitor (reaction 2).

Both in the case of reaction 1 and in the case of reaction 2, the enzyme reaction was monitored by fluorescence spectroscopy (328 nm (extinction)/393 nm (emission)) after 10 µl of a 3% (v/v) aqueous solution of dimethyl sulfoxide containing 0.075 mmol of the substrate/l had been added.

The enzyme activity was expressed in increase in extinction/minute.

The inhibitor effect was calculated as a percentage inhibition in accordance with the following formula:

% inhibition=100−[(increase in extinction/minute in reaction 2)/(increase in extinction/minute in reaction 1)×100].

The IC$_{50}$, that is the inhibitor concentration which is required for 50% inhibition of the enzyme activity, was determined graphically by plotting the percentage inhibitions at different inhibitor concentrations.

The buffer solution contained 0.05% Brij (Sigma, Deisenhofen, Germany) and also 0.1 mol of Tris/HCl/l, 0.1 mol of NaCl/l, and 0.01 mol of CaCl$_2$/l (pH=7.5). The enzyme solution contained 1.67 µg of the enzyme domain/ml. The substrate solution contained 0.075 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH$_2$ (Bachem, Heidelberg, Germany)/l.

Determining the enzymatic activity of the catalytic domain of human gelatinase-A (MMP-2). This protein was obtained as inactive proenzyme from INVITEK, Berlin (catalog No. 30 100 602).

Activation of the Proenzyme:

2 parts by volume of proenzyme were incubated, at 37° C. for 0.5 hour, with 1 part by volume of APMA solution. The APMA solution was prepared from a 10 mmol/l p-aminophenylmercuric acetate solution in 0.1 mmol/l NaOH by diluting with 3 parts by volume of Tris/HCl buffer pH 7.5 (see below). The pH was adjusted to between 7.0 and 7.5 by adding 1 mmol HCl/l. After the enzyme had been activated, it was diluted with the Tris/HCl buffer down to a concentration of 0.83 µg/ml. In order to measure the enzyme activity, 10 µl of enzyme solution were incubated, for 15 minutes, with 10 µl of a 3% (v/v) buffered solution of dimethyl sulfoxide (reaction 1). In order to measure the enzyme inhibitor activity, 10 µl of enzyme solution were incubated with 10 µl of a 3% (v/v) buffered solution of dimethyl sulfoxide which contained the enzyme inhibitor (reaction 2).

Both in the case of reaction 1 and in the case of reaction 2, the enzyme reaction was monitored by fluorescence spectroscopy (328 nm (extinction)/393 nm (emission)) after 10 µl of a 3% (v/v) aqueous solution of dimethyl sulfoxide containing 0.3 mmol of the substrate/l had been added.

The enzyme activity was expressed as increase in extinction/minute.

The inhibitor effect was calculated as a percentage inhibition in accordance with the following formula:

% inhibition=100−[(increase in extinction/minute in reaction 2)/(increase in extinction/minute in reaction 1)×100].

The IC$_{50}$, that is the inhibitor concentration which is required for 50% inhibition of the enzyme activity, was determined graphically by plotting the percentage inhibitions at different inhibitor concentrations.

The buffer solution contained 0.05% Brij (Sigma, Deisenhofen, Germany) and also 0.1 mol of Tris/HCl/l, 0.1 mol of NaCl/l and 0.01 mol of CaCl$_2$/l (pH=7.5). The enzyme solution contained 0.83 µg of the enzyme domain/ml. The substrate solution contained 0.3 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH$_2$ (Bachem, Heidelberg, Germany)/l.

Determining the enzymatic activity of the catalytic domain of human gelatinase-B (MMP-9). This protein was obtained as inactive proenzyme from Roche, Mannheim (catalog No. 1 758 896).

Activation of the Proenzyme:

2 parts by volume of proenzyme were incubated, at 37° C. for 4 hours, with 1 part by volume of APMA solution. The APMA solution was prepared from a 10 mmol/l p-aminophenylmercuric acetate solution in 0.1 mmol/l NaOH by diluting with 3 parts by volume of Tris/HCl buffer, pH 7.5 (see below). The pH was adjusted to between 7.0 and 7.5 by adding 1 mmol/l HCl. After the enzyme had been activated, it was diluted with the Tris/HCl buffer down to a concentration of 4.2 mU/ml.

In order to measure the enzyme activity, 10 µl of enzyme solution were incubated, for 15 minutes, with 10 µl of a 3% (v/v) buffered solution of dimethyl sulfoxide (reaction 1). In order to measure the enzyme inhibitor activity, 10 µl of enzyme solution were incubated with 10 µl of a 3% (v/v) buffered solution of dimethyl sulfoxide which contained the enzyme inhibitor (reaction 2).

Both in the case of reaction 1 and in the case of reaction 2, the enzyme reaction was monitored by fluorescence spectroscopy (328 nm (extinction)/393 nm (emission)) after 10 µl of a 3% (v/v) aqueous solution of dimethyl sulfoxide containing 0.15 mmol of the substrate/l had been added.

The enzyme activity was expressed as increase in extinction/minute.

The inhibitor effect was calculated as a percentage inhibition in accordance with the following formula:

% inhibition=100−[(increase in extinction/minute in reaction 2)/(increase in extinction/minute in reaction 1)×100].

The IC$_{50}$, that is the inhibitor concentration which is required for 50% inhibition of the enzyme activity, was determined graphically by plotting the percentage inhibitions at different inhibitor concentrations.

The buffer solution contained 0.05% Brij (Sigma, Deisenhofen, Germany) and also 0.1 mol of Tris/HCl/l, 0.1 mol of NaCl/l and 0.01 mol of CaCl$_2$/l (pH=7.5). The enzyme solution contained 4.2 mU of the enzyme domain/ml. The substrate solution contained 0.15 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH$_2$ (Bachem, Heidelberg, Germany)/l.

Table 2 below shows the results.

TABLE 2

| Example | MMP-1 IC$_{50}$ [nM] | MMP-2 IC$_{50}$ [nM] | MMP-3 IC$_{50}$ [nM] | MMP-8 IC$_{50}$ [nM] | MMP-9 IC$_{50}$ [nM] | MMP-13 IC$_{50}$ [nM] |
|---|---|---|---|---|---|---|
| 1 | 700 | 2.5 | 70 | 13 | 3.5 | 6.3 |

The invention claimed is:
1. A compound of the formula I wherein
A is covalent bond or —(C$_1$-C$_4$)-alkylene;
B, D and E are independently
  covalent bond,
  —(C$_{1-4}$)-alkylene or
  -B1-B2-B3-;
B1 is —(CH$_2$)$_v$—;
B3 is —(CH$_2$)$_m$—;
B2 is
  —C(=O)—
  —(C$_2$-C$_4$)-alkenylene,
  —(C$_2$-C$_4$)-alkynylene,
  —S(=O)$_o$—,
  —N(R6)—,
  —N(R6)—C(=Y)—,
  —C(=Y)—N(R6)—,
  —N(R6)—SO$_2$—,
  —SO$_2$—N(R6)—,
  —N(R6)—SO$_2$—N(R6)—,
  —N(R6)—C(=Y)—N(R6)—,
  —O—C(=O)—N(R6)—,
  —NH—C(=O)—O—,
  —O—,
  —C(=O)—O—,
  —O—C(O)—,
  —O—C(O)—O—,
  —O—CH$_2$—C(=O)—,
  —O—CH$_2$—C(=O)—O—,
  —O—CH$_2$—C(=O)—N(R6)—,
  —C(=O)—CH$_2$—O—,
  —O—C(=O)—CH$_2$—O—,
  —N(R6)—C(=O)—CH$_2$—O—,
  —O—(CH$_2$)$_s$—O—,
  —O—(CH$_2$)$_t$—N(R6)—,
  —N(R6)—(CH$_2$)$_u$—O—,
  —N(R6)—N(R6)—,
  —N=N—,
  —N(R6)—CH=N—,
  —N=CH—N(R6)—,
  —N(R6)—C(R7)=N—,
  —N=C(R7)—N(R6)—, or
  —(C$_2$-C$_6$)—alkynylene;
v and m are each independently zero, 1 or 2, provided that that the sum of v and m is zero, 1 or 2;
R6 is hydrogen atom, methyl or ethyl;
Y is oxygen atom or sulfur atom;
o is zero, 1 or 2;
s is 2 or 3;
t is 2 or 3;
u is 2 or 3;
R7 is —NH—R6;
ring1, ring2 or ring3 are independently
  covalent bond,
  —(C$_6$-C$_{14}$)-aryl optionally substituted independently one, two or three times by G, or
  4- to 15-membered Het ring optionally substituted independently one, two or three times by G;
ring4 is
  —(C$_6$-C$_{14}$)—aryl optionally substituted independently one, two or three times by G,
  4- to 15-membered Het ring optionally substituted independently one, two or three times by G, or
  radical selected from wherein the radical is optionally substituted one time by G;
G is
  hydrogen atom,
  halogen,
  =O,
  —(C$_1$-C$_6$)-alkyl optionally substituted independently one, two or three times by halogen, —(C$_3$-C$_6$)-cycloalkyl, —(C$_2$-C$_6$)-alkynyl, —(C$_6$-C$_{14}$)-aryl or Het ring,
  —(C$_6$-C$_{14}$)-aryl,
  Het ring,
  —C(=O)—O—R10,
  —C(=S)—O—R10,
  —C(=O)—NH—R11,
  —C(=S)—NH—R11,
  —O—R12,
  —C(=O)—R10,
  —S(=O)$_p$—R12,
  —NO$_2$,
  —CN,
  —N(R15)—R12, or
  —SO$_2$—N(R12)—R16;
R10 is
  —(C$_1$-C$_6$)-alkyl optionally substituted independently one or two times by —(C$_3$-C$_6$)-cycloalkyl, —(C$_2$-C$_6$)-alkynyl, —(C$_6$-C$_{14}$)-aryl or Het ring,
  —(C$_6$-C$_{14}$)-aryl or
  Het ring;

R11 is
—(C₁-C₆)-alkyl optionally substituted independently one or two times by —(C₃-C₆)-cycloalkyl, —(C₂-C₆-)-alkynyl, —(C₆-C₁₄)-aryl or Het ring, or
—(C₆-C₁₄)-aryl or
Het ring;

R12 is
hydrogen atom,
—(C₁-C₆)-alkyl optionally substituted independently one, two or three times by halogen, —(C₃-C₆)-cycloalkyl, —(C₂-C₆)-alkynyl, —(C₆-C₁₄)-aryl or Het ring,
—(C₆-C₁₄)-aryl,
Het ring,
—C(=O)—O—R13,
—C(=S)—O—R13,
—C(=O)—NH—R14, or
—C(=S)—NH—R14;

R13 is
—(C₁-C₆)-alkyl optionally substituted independently one or two times by —(C₃-C₆)-cycloalkyl, —(C₂-C₆)-alkynyl, —(C₆-C₁₄)-aryl, or Het ring,
—(C₆-C₁₄)-aryl or
Het ring;

R14 is
—(C₁-C₆)-alkyl optionally substituted independently one or two times by —(C₃-C₆)-cycloalkyl, —(C₂-C₆)-alkynyl, —(C₆-C₁₄)-aryl or Het ring,
—(C₆-C₁₄)-aryl or
Het ring;

p is zero, 1 or 2;

R15 is
hydrogen atom,
—(C₁-C₆)-alkyl, or
—SO₂—(C₁-C₆)-alkyl wherein the alkyl is optionally substituted by one or two times by —(C₃-C₆)-cycloalkyl, —(C₂-C₆)-alkynyl, —(C₆-C₁₄)-aryl or Het ring;

R16 is
hydrogen atom,
—(C₁-C₆)-alkyl optionally substituted independently one or two times by —(C₃-C₆)-cycloalkyl, —(C₂-C₆)-alkynyl, —(C₆-C₁₄)-aryl or Het ring,
—C(=O)—O—R8,
—O—R8, or
—(C₃-C₆)-cycloalkyl;

X is NH—OH;
n is 1;

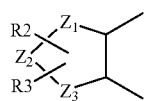

as the constituent structure of the compound is an unsaturated or partially saturated ring containing 5 ring atoms, where Z1, is a sulfur atom and Z2 and Z3 are carbon atoms that are substituted by
R2 and R3 form, together with the carbon atoms through which they are bonded, a
phenyl ring optionally substituted independently one or two times by G;

R8 is
hydrogen atom,
—(C₁-C₆)-alkyl optionally substituted independently one or two times by —(C₃-C₆)-cycloalkyl, —(C₂-C₆)-alkynyl, —(C₆-C₁₄)-aryl, or Het ring, or one, two, three, four or five times by fluorine,
—(C₆-C₁₄)-aryl or
Het ring;

Y1 is OH; and
Y2 is H, or
a stereoisomeric form thereof, mixture of stereoisomeric forms, in any ratio, or a salt thereof.

2. The compound of the formula I according to claim 1, wherein ring1, ring2 or ring3 are independently
covalent bond,
phenyl, naphthyl, 1-napthyl, 2-naphthyl, anthryl or fluorenyl, which is optionally substituted independently one, two or three times by G, or
4- to 15-membered Het ring selected from acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolylidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl, which is optionally substituted independently one, two or three times by G;

ring4 is
—(C₆-C₁₄)-aryl selected from phenyl, naphthyl, 1-naphthyl, 2-naphthyl, anthryl and fluorenyl, which is optionally substituted independently one, two or three times by G,
4- to 15-membered Het ring selected from acridinyl, azepinyl, azetidinyl, aziridinyl, benzimidazalinyl, benzimidazolyl, benzofuranyl, benzothiofuranyl, benzothiophenyl, benzoxazolyl, beuzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenandirolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl, which is optionally substituted independently one, two or three times by G, or radical selected from

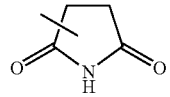 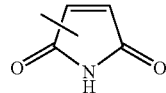

wherein the radical is optionally substituted one time by G, or a stereoisomeric form thereof, mixture of stereoisomeric forms, in any ratio, or a salt thereof.

3. The compound of the formula I according to claim 1, wherein

B, D and E are independently
covalent bond,
—($C_1$-$C_2$)-alkylene or
—B1-B2-B3-;

B2 is
ethenylene,
ethynylene,
—C(=O)—
—N(R6)—C(=O)—,
—C(=O)—N(R6)—,
—O— or
—S—;

ring1, ring2 or ring3 are independently,
covalent bond,
phenyl or naphthyl, which is optionally substituted independently one or two times by G, or
Het ring selected from dihydrofuranyl, furanyl, pyridyl, pyrimidinyl, pyrrolyl, thiadiazolyl, thiazolyl and thiophenyl, which is optionally substituted independently one or two times by G;

ring4 is
phenyl or naphthyl, which is optionally substituted independently one or two times by G,
Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, or radical

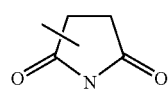

which is optionally substituted once by G;

G is
hydrogen atom,
Br, Cl or F,
—($C_1$-$C_4$)-alkyl optionally is substituted independently one or two times by F, phenyl, cyclopropyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
phenyl,
Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
—C(=O)—O—R10,
—C(=O)—NH—R11,
—O—R12
—C(=O)—R10,
—S(=O)$_p$—R12,
—NO$_2$,
—CN or
—N(R15)—R12;

R10 is
—($C_1$-$C_6$)-alkyl optionally substituted independently one or two times by cyclopropyl, phenyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,
phenyl, or
Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;

R11 is
—($C_1$-$C_6$)-alkyl optionally substituted independently one or two times by cyclopropyl, phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, phenyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;

R12 is hydrogen atom,

—($C_1$-$C_6$)-alkyl optionally substituted independently one, two or three times by halogen, cyclopropyl, phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, phenyl, Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G,

—C(=O)—O—R13,

—C(=S)—O—R13, or

—C(=O)—NH—R14;

R13 is

—($C_1$-$C_6$)-alkyl optionally substituted independently one or two times by cyclopropyl, phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, phenyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;

R14 is

—($C_1$-$C_6$)-alkyl optionally substituted independently one or two times by phenyl or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G, phenyl, or Het ring selected from benzofuranyl, dihydrofuranyl, dibenzofuranyl, dibenzothiophenyl, furanyl, morpholinyl, piperazinyl, piperidyl, pyridinyl, pyrimidyl, pyridothiophenyl, pyrrolyl, pyrrolidinyl, thiazolyl and thiophenyl, which is optionally substituted independently one or two times by G;

p is 1 or 2;

R15 is hydrogen atom or

—($C_1$-$C_6$)-alkyl, or a stereoisomeric form thereof, mixture of stereoisomeric forms, in any ratio, or a salt thereof.

4. The compound of formula I according to claims 1, wherein

A is a covalent bond or —$CH_2$—$CH_2$—,

B, D and E are independently covalent bond,

—($C_1$-$C_2$)-alkylene or

-B1-B2-B3-;

B2 is

—C(=O)— ethynylene,

—S—,

—N(R6)—C(=O)—,

—C(=O)—N(R6)—, or

—O—;

R6 is hydrogen atom ring1, ring2 or ring3 are independently, covalent bond, phenyl which is optionally substituted independently one or two times by G, or Het ring is selected from furanyl, pyridyl, pyrimidinyl and thiophenyl, which is optionally substituted independently one or two times by G, ring4 is phenyl and is optionally substituted independently one or two times by G, Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, or radical

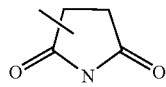

wherein the radical is optionally substituted independently one time by G,;

G is hydrogen atom,

Br, Cl or F,

—($C_1$-$C_4$)-alkyl optionally substituted independently one, two or three times by Br, Cl, F, —$C_3$—, cycloalkyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl, Het ring selected from benzofuranyl, dibenzofuranyl, furanyl morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,

—C(=O)—O—R10,

—C(=O)—NH—R11,

—O—R12,

—C(O)—R10,

—S(O)$_p$—R12,

—$NO_2$,

—CN or

—N(R15)—R12;

R10 is
- —($C_1$-$C_6$)-alkyl optionally substituted independently one or two times by cyclopropyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,
- phenyl, or
- Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G;

R11 is
- —($C_1$-$C_6$)-alkyl optionally substituted independently one or two times by cyclopropyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, phenyl, or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G;

R12 is
- hydrogen atom,
- —($C_1$-$C_6$)-alkyl optionally substituted independently one, two or three times by halogen, cyclopropyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,
- phenyl,
- Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,
- —C(=O)—O—R13
- —C(=S)—O—R13, or
- —C(=O)—NH—R14;

R13 is
- —($C_1$-$C_6$)-alkyl optionally substituted independently one or two times by cyclopropyl, phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,
- phenyl or
- Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G, R14 is
- —($C_1$-$C_6$)-alkyl optionally substituted independently one or two times by phenyl or Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G,
- phenyl or
- Het ring selected from benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl and thiophenyl, which is optionally substituted independently one or two times by G;

p is zero, 1 or 2;

R15 is
- hydrogen atom or
- —($C_1$-$C_6$)-alkyl, or a stereoisomeric form thereof, mixture of stereoisomeric forms, in any ratio, or a salt thereof.

5. The compound of the formula I according to claim 1, which is N-(hydroxy)-2-(4'-chlorobiphenyl-4-sulfonyl)-4-hydroxy-1,2,3,4-tetrahydrobenzo[4,5]thieno[3,2-c]pyridine-1-carboxamide, or a salt thereof.

* * * * *